United States Patent [19]

Apicella et al.

[11] Patent Number: 5,273,040
[45] Date of Patent: Dec. 28, 1993

[54] MEASUREMENT OF VETRICLE VOLUMES WITH CARDIAC MRI

[75] Inventors: Anthony Apicella, Willoughby; Christopher H. Wood, Cleveland; Moriel S. NessAiver, Cleveland Heights, all of Ohio

[73] Assignee: Picker International, Inc., Highland Hts., Ohio

[21] Appl. No.: 791,855

[22] Filed: Nov. 14, 1991

[51] Int. Cl.$^5$ ............................................. A61B 5/055
[52] U.S. Cl. ........................... 128/653.2; 364/413.13; 382/6; 382/18; 382/22; 128/695
[58] Field of Search ................. 128/653.1, 653.2, 695; 382/6, 18, 22; 364/413.13, 413.16, 413.18; 358/111

[56] References Cited

U.S. PATENT DOCUMENTS

| | | | |
|---|---|---|---|
| 4,295,473 | 10/1981 | Diamond et al. | 128/695 |
| 4,637,400 | 1/1987 | Marcus | 128/653.1 |
| 4,716,904 | 1/1988 | Meno | 128/654 |
| 4,777,957 | 10/1988 | Wehrli et al. | 128/653.3 |
| 4,961,425 | 10/1990 | Kennedy et al. | 128/653.1 |
| 5,072,384 | 12/1991 | Doi et al. | 382/6 |
| 5,092,335 | 3/1992 | LeBihan | 128/653 |
| 5,119,439 | 6/1992 | Osawa et al. | 382/22 |
| 5,170,440 | 12/1992 | Cox | 382/22 |

FOREIGN PATENT DOCUMENTS

312427A3  4/1989  European Pat. Off. .

OTHER PUBLICATIONS

Automated Segmentation of Cardiac MR Images, 1990, M. Bister, et al.; Free University of Brussels; IRIS Research Group, Belgium.
Probabilistic Segmentation of Myocardial Tissue by Deterministic Relaxation, 1990, Broekhuijsen, et al.; Dept. of Computer Science, Brigham Young University, Utah.
A System for Knowledge-Based Boundary Detection of Cardiac Magnetic Resonance Image Sequences; Suh, et al.; School of Electrical Engineering, Georgia Institute of Technology/Imaging Science Laboratory, Emory University Hospital, 1990.
A Relaxation Algorithm for Segmentation of the Endocardial Surface from Cine CT; Barrett, et al.; Dept. of Computer Science, Brigham Young University, 1990.

*Primary Examiner*—Lee S. Cohen
*Assistant Examiner*—K. M. Pfaffle
*Attorney, Agent, or Firm*—Fay, Sharpe, Beall, Fagan, Minnich & McKee

[57] ABSTRACT

A first image (20) and a second image (22) are taken through the patient's heart region at small time displaced intervals. The first and second images are subtracted (24) to generate a difference image which is indicative of the tissue which has moved during the short time interval, i.e. the boundary of the ventricles. Voxels from regions outside the boundary are adjusted to remove lung tissue (40), and ventricle boundary or edge voxels (48) and analyzed to generate a non-blood tissue histogram (62). Voxels within the boundary are analyzed to generate a blood tissue histogram (60). The histograms are fit (66, 74) to smooth curves which represent the probability distribution or confidence that each voxel value represents blood or non-blood tissue. Contiguous voxels within the boundary are counted (96) and adjusted for voxel size (98) to create an indication of left and right ventricle volume (100l, 100r). In the preferred embodiment, the ventricle volume is determined by summing the confidence value that each voxel within the boundary represents blood.

28 Claims, 3 Drawing Sheets

MEASUREMENT OF VETRICLE VOLUMES WITH CARDIAC MRI

BACKGROUND OF THE INVENTION

The present invention pertains to the medical diagnostic arts. It finds particular application in conjunction with identifying and quantizing the ventricular volumes in a patient's heart from magnetic resonance image data and will be described with particular reference thereto. It is to be appreciated, however, that the invention may also find application in conjunction with identifying other regions of human or non-human subjects, determining a volume of identified regions, and the like, with either magnetic resonance or other imaging modalities.

Heretofore, ventricular volumes have been determined by first generating a volumetric image representation of a rectangular portion of the patient's body that includes the heart. Commonly, the volume image representation included a plurality of parallel planar or slice images which were coordinated with the cardiac cycle such that each slice or plane was taken at or near the same cardiac phase. A trained radiologist or technician viewed each slice and marked the edges of the ventricles. Once the boundary of the ventricle regions was marked, the volume could be readily calculated. For example, the number of voxels in the volume within the boundary or the number of voxels of each slice within the boundary could be counted. From the dimensions of the voxel or the dimensions of the voxels and the interslice spacing, the volume was readily calculated. Not only did this technique require a large amount of time, but the results were not reproduceable. Each radiologist or other trained expert tended to define the edges of the ventricles differently.

Various automatic methods have been proposed for determining the ventricular volumes without human assistance. Because the blood and the tissue have different gray scale or intensity, one could use this difference to determine the boundary. Boundaries or edges of the magnetic resonance image are characterized by high frequency components. Noise, motion, and other artifacts are present at all frequencies but most significant in the high frequency components. This noise created uncertainty in the location of the interface. In one approach, a contour following algorithm was applied to the image to make a first approximation of the boundary of the ventricle in each slice. Density profiles on either side of the proposed border were examined and the contour following algorithm was reapplied. This procedure was repeated iteratively until a stable threshold was obtained. This iterative approach was not only time consuming and computationally expensive, but tended to have inaccuracies arising from the inclusion of surrounding tissue other than ventricles in the process.

Another drawback to this method is that it assumed that the intensity profile passing through the heart/blood interface was sigmoidal, with the optimal edge position existing at voxels having the largest gradient. This assumption is unsupported. When the intensity profile is not sigmoidal, there are errors in the estimate of the cardiac volume.

In a second technique, a threshold was used to create a binary image from the volume image. That is, the intensity or gray scale of each voxel was examined and compared with a threshold. Based on this comparison, each pixel or voxel was classified as blood, hence an interior region of the ventricle, or non-blood. Identifying the threshold value commonly required an initial human guess. The guess was iteratively adjusted in repetitions of the binary image forming process until appropriate results were achieved. This technique was again slow and computationally burdensome.

Another technique used a priori probabilities for the expected tissue classes within the volume to produce an initial segmentation of the image, i.e. define the ventricle boundaries. These probabilities were updated in accordance with the initial image and the segmentation process repeated with the updated probabilities. This process was iteratively repeated until the segmentation reached a steady state. This technique required some manual segmentation to create a training set and to determine the initial probabilities. Moreover, modifying the decision criteria, i.e. the probabilities, based on results tended to perpetuate inaccuracies.

In another approach, each voxel was classified based on its gray scale level, gradient, and location. The voxel classifications were iteratively updated in order to make the relative classifications more consistent using the Dempster-Schafer theory of knowledge. This technique again required a priori information and was computationally excessive. Moreover, because the iterations were based on prior iterations, errors were compounded.

The present invention contemplates a new and improved voluming technique which overcomes the above-referenced problems and others.

SUMMARY OF THE INVENTION

In accordance with the present invention, ventricle or other volumes of a subject are determined with a three step process. First, the edges of the ventricle or region of interest are determined. Second, portions of the image outside of the identified edges is classified as tissue and a selected portion of the data inside edges are classified as blood. The distribution of blood and tissue image intensities is fit to a pair of smooth curves which indicate the probability that a voxel of a given intensity is blood or tissue. Third, the contiguous voxels indicated as containing blood are counted or summed. The number of voxels is adjusted with the voxel size to indicate the volume of the ventricle or other region of interest.

In accordance with a more limited aspect of the present invention, the first step of determining the edges of the ventricle includes collecting at least two images of the heart. The first image is at the selected point of the cardiac circle and the second image is slightly time displaced from the first. Provided the two images are close in time, they will be substantially identical, except that the heart periphery will have expanded (or contracted) slightly. These two images are subtracted zeroing all but a ring around the ventricles (or other moving tissue).

In accordance with another more limited aspect of the present invention, the second step includes comparing the intensity of each voxel to the two probability curves to determine the probability that each voxel represents blood or non-blood tissue.

In accordance with another more limited aspect of the present invention, in the third step, the value of each voxel is weighted in accordance with the probability that it represents blood.

In accordance with another aspect of the present invention, the non-blood voxels are divided into voxels representing lung and non-lung tissue. The data representing the lung tissue is eliminated such that the probability curves are based on blood intensities and on non-lung, non-blood tissue intensities.

One advantage of the present invention resides in its fast and simple, yet accurate segmentation.

Another advantage of the present invention resides in the improved accuracy. Eliminating lung and uncertain edge values before determining the criteria for classifying a voxel as blood and non-blood eliminates a major source of error in the resultant images.

Another advantage of the present invention is that it produces accurate results even with noisy images. Making voxel classification decisions based on a histogram as opposed to individual voxel properties improves overall reliability.

Other advantages of the present invention reside in its improved processing speed and reduced complexity. Iterative data analysis is eliminated, as are training sets and the inputting of a priori information or a knowledge base.

Still further advantages will become apparent to those of ordinary skill in the art upon reading and understanding the following detailed description of the preferred embodiment.

BRIEF DESCRIPTION OF THE DRAWINGS

The invention may take form in various parts and arrangements of parts and in various steps and arrangement of steps. The drawings are only for purposes of illustrating a preferred embodiment and are not to be construed in limiting the invention.

DETAILED DESCRIPTION OF THE PREFERRED EMBODIMENT

Figure 1A:
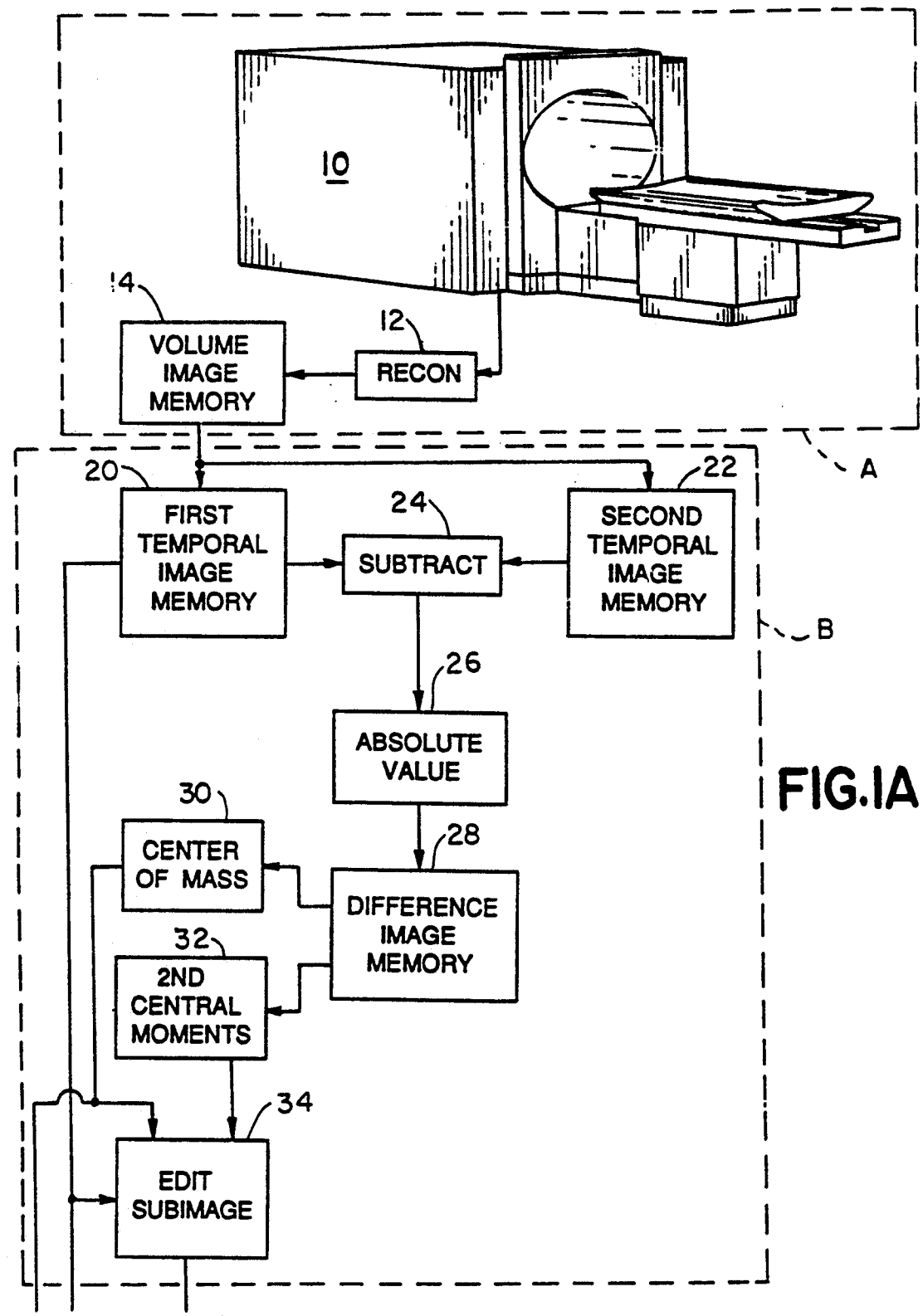
FIGS. 1A and 1B taken together are a diagrammatic illustration of the present invention.
Figure 1B:
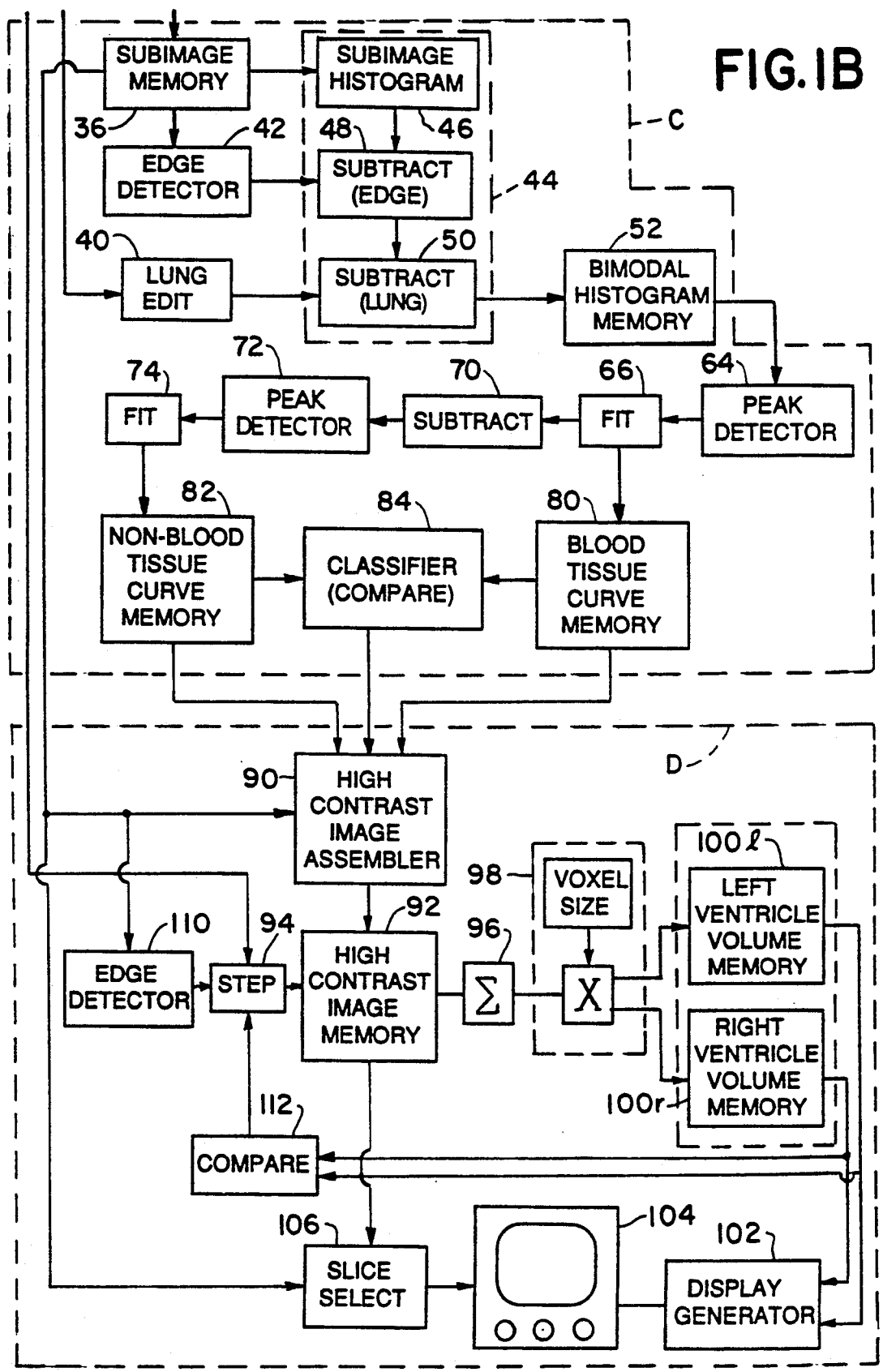

With reference of FIGS. 1A and 1B, a magnetic resonance imaging apparatus A, examines a selected region of a subject and generates a volume image representation thereof. More specifically to the preferred embodiment, the volume image representation, preferably the heart and surrounding areas, is a product of a black blood cine sequence in which the volume is defined by a plurality of parallel slices. A motion detection means B locates the region of interest, in the preferred embodiment the region of the ventricles. A segmentation means C parametrically determines intensity ranges of voxels of the image representation in a blood intensity range and voxels in a non-blood tissue intensity range. A region growing means D collects or counts contiguous image voxels which have the intensity of blood volume of the image representation.

The magnetic resonance data acquisition means A includes a conventional magnetic resonance scanner 10. The magnetic resonance scanner includes the appropriate coils and supporting electronics for generating a substantially uniform main magnetic field through an imaging field. Radio frequency coils and supporting electronics selectively introduce radio frequency pulses into the examination region to induce resonance of selected bipoles and to manipulate the induced resonance. Gradient field coils and supporting electronic apply gradient field pulses across the examination region to provide phase and frequency encoding in the excited resonance and for defining slices or volumes.

Magnetic resonance echoes or other diagnostic data is collected and reconstructed by a reconstruction means 12 into the volume image representation which is stored in an appropriate volume image memory 14. The reconstruction means 12 reconstructs a series of two dimensional slices which taken together define the volume. Alternately, a three dimensional reconstruction algorithm may be used. In the preferred black blood cine sequence, blood tissue appears at one intensity extreme, the intensity extreme which is commonly displayed as black on a black and white monitor. Non-blood tissue contributions to the image tend to be near the other intensity extreme, the intensity extreme which is generally displayed as white. Preferably, the black blood cine technique is used to generate a plurality of planes collected at the same point of the cardiac cycle. Obtaining high temporal resolution is attained by using cardiac gating. That is, the patient's cardiac cycle is monitored and the MRI scan commences a preselected duration after the R-wave or other characteristic portion of the cardiac cycle. Multiple measurements (up to 64) are acquired at a fixed interval (typically 10–25 msec). The preferred black blood cine sequence results in temporal resoluation of 20 msec. which allows for 40 images covering 80% of a typical 1000 msec. R—R interval. Optionally, CT or other data acquisition means may be utilized.

The motion detecting means B causes two temporally adjacent images to be generated. That is, the black blood cine sequence is used to generate the same spatial volume, but offset a very short time interval. The second MRI scan is triggered a duration after the R-wave which is slightly longer (or shorter) than the duration after the R-wave at which the first image was generated. The motion means B includes a first memory means 20 for storing a first temporal image and a second temporal memory means 22 for storing a second temporal image. The first and second memory means are preferably portions of a large RAM or disc memory. A subtracting means 24 subtracts corresponding voxels of the two images generating a temporal difference image. Because the first and second temporally displaced images are taken very close together in time, they are essentially identical, except in areas of movement. The movement, of course, is primarily in the ventricles. Thus, the difference image is essentially blank, except for a dark line around the ventricles, which dark line has a width which substantially corresponds to the amount of cardiac movement in the time between the first and second images. An absolute value means 26 compares the absolute value of each voxel of the difference image with a preselected threshold value selected to differentiate between the differential ventricle movement surface or band line and stray differences. Small values are set to zero and other values are set to one. Optionally, an additional algorithm may be incorporated for discarding voxels which are remote from the contiguous surface of voxels surrounding the ventricles. The absolute value of the difference image is stored in a difference image memory means 28.

The center of mass of the temporal difference image falls at or near the boundary between the left and right ventricles in a short axis view of a normal human heart. The second central moments of the difference image correlates directly to how large a subimage is necessary in order to contain just the heart. A center of mass means 30 determines the center of mass or geometric center from the temporal difference image. A second moment means 32 calculates the second moments of the difference image. An editing means 34 edits the original volume image, slice by slice, from the first temporal image memory means 20 to produce a square cross section subimage which contains substantially just the heart. That is, the subimage 36 is centered at the center of mass of the difference image and has side lengths equal to the root of the second central moments of the difference image at the largest cross section of the heart. Optionally, the center and image size information can be used to reformat the MRI sequence to limit the examination region to the subimage region.

The segmentation means C, in the preferred embodiment, segments or identifies three types of tissue—blood, lung, and other types of non-blood tissue. Prior to the determination of probabilities, a lung editing means 40 examines the voxels of the original volume image in memory 20 to locate the lung region. Prior to computation of the histogram, all voxels in the lung region are excluded from the computation. Lung location is determined by region growing to collect background voxels over the entire images. The largest regions are along the left and right sides of the patient and the next largest region is the cavity containing the lung. An edge detection means 42 detects edge voxels corresponding to edge regions in the selected subimage in the subimage memory means 36. An edge image is computed by passing a sobel operator over the subimage and thresholding the results. The resulting histogram now contains primarily information related to blood and tissue only. This gives a strong binomial flavor and assists in clustering the histogram to determine probabilities for blood and tissue.

A subimage histogram means 44 generates a histogram, i.e. intensity versus number of voxels, for voxels in the blood region and in the non-blood, non-lung, non-edge region. More specifically, a subimage histograms means 46 determines the intensity corresponding to each voxel of the subimage stored the subimage memory 36. An edge voxel subtracting means 48 subtracts or deletes the contributions from the edge voxels as determined by the edge detection means 42. In this manner, voxels which contain part blood and part non-blood tissue are excluded from being part of the basis of the projected probabilities. Analogously, a lung voxel subtracting means 50 subtracts or deletes the contribution of the voxels or voxels identified by the lung region identifying means 40 as being lung tissue. A bimodal histogram memory means 52 stores the histogram of voxel intensity versus number of occurrences of the blood and of the non-blood, non-lung, non-edge voxels.

Figure 2:
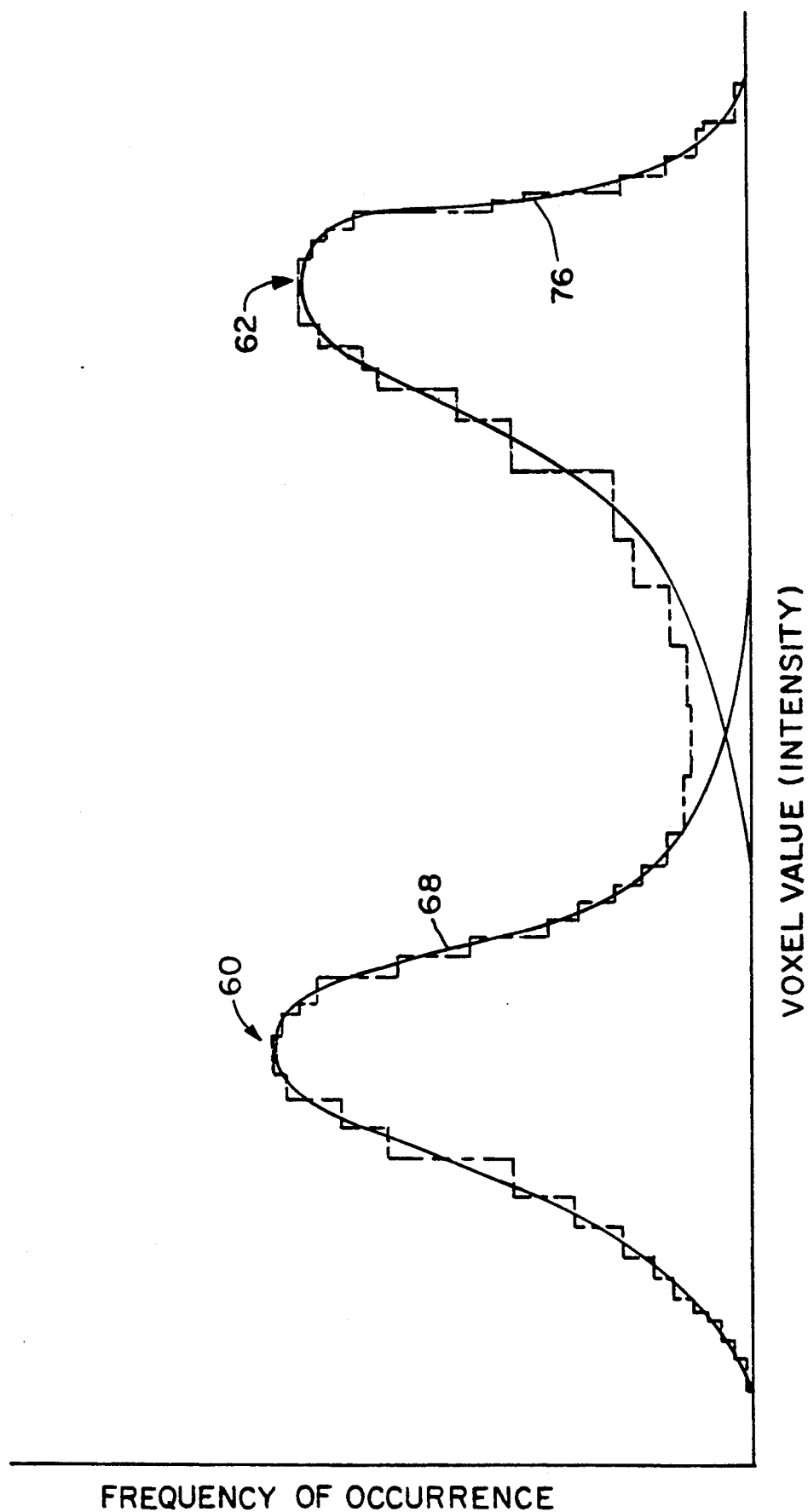
FIG. 2 illustrates exemplary blood and non-blood tissue probability curves.

With continuing reference to FIGS. 1A and 1B and further reference to FIG. 2, the histogram define a curve with two peaks, one peak 60 corresponding to the average blood tissue intensity and the other peak 62 centered around the average non-blood (non-lung, non-edge) tissue intensity. The low or black intensity cluster of voxels represents blood and the high or light intensity cluster represents non-blood tissue. A first peak detector 64 detects one of the peaks, e.g. the blood cluster. A first curve fitting means 66 fits a smooth curve to the blood peak of the histogram. In the preferred embodiment, the curve fitting means 66 fits the blood peak to a first Gaussian curve 68. The intensity level occurring most frequently in the histogram is used as the initial estimate of the mean Gaussian distribution. The frequency of occurrence of the initial estimate of the amplitude and the initial estimate of the variance is estimated by tracking amplitude in the vicinity of the peak in both directions. An amplitude decrease by a factor of e, the base of naperian logarithms, marks the variance. These initial estimates of the mean and variance are entered into a non-linear least squares fit routine to estimate the Gaussian curve best representing the blood peak. A subtracting means 70 subtracts the blood tissue Gaussian curve from the bimodal histogram in the vicinity of the blood peak. A second peak detector means 72 detects the non-blood cluster peak. A second curve fitting means 74 fits a second Gaussian curve 76 to the non-blood tissue peak.

Of course, other curve fitting routines may also be used. Other appropriate curves for fitting to the histogram include:

$$\text{lognormal} = \frac{1}{x} e^{-ln^2 x/2} \quad (1)$$

$$\text{Maxwell } x^2 e^{x^2}/2 \quad (2)$$

$$\text{Erlang } x^r e^{-x} \quad (3)$$

$$\text{Cauchy } 1/(1+x^2) \quad (4)$$

$$\text{Normal } e^{-x/2} \quad (5)$$

$$\text{Beta } x^b(1-x)^c \quad (6)$$

and the like. The best fit blood histogram curve is stored in a blood tissue curve memory so and the best fit tissue histogram curve is stored in a non-blood tissue histogram memory 82. The blood and tissue best fit curves represent the probability that each voxel represents blood or tissue. That is, the amount of deviation between the intensity of a voxel and the peak of the blood curve or the tissue curve is indicative of the probability that the voxel represents blood or tissue, respectively. The best fit curves 68, 76 are preferably determined based on a single slice of the volume image. The determined probability curves are valid for other slices of the volume.

A classification means 84 compares each available voxel intensity with the probability curves 68, 76 and classifies the voxel as either blood or non-blood tissue and the probability or certainty of the classification. That is, the apex of each of Gaussian curves 68 and 76 is set equal to one, i.e. 100% probability. For each intensity, the probability that it represents blood or non-blood tissue is indicated by the probability curve. If a given intensity has a higher probability on the blood curve than on the non-blood curve, it is classified as blood tissue. If a given intensity has a higher probability on the non-blood curve than the blood curve, it is classified as non-blood tissue.

The region growing means D includes a high contrast or blood image forming means 90 which determines the classification of each voxel of the subimage. More specifically, it consults the classification means 84 with the intensity of each voxel to determine whether the voxel represents blood or non-blood tissue. If the intensity represents non-blood tissue, a zero value is assigned to that voxel. If the intensity is classified as blood tissue, then the blood image forming means 90 consults the probability distribution curve memory means so to determine the confidence with which the corresponding intensity was classified as blood. Again, the apex of the best fit curve is classified as one or a 100% confidence value. Values further down the curve from the peak have a correspondingly lower confidence value. In the preferred embodiment, each voxel which is determined to represent blood, is assigned the corresponding confidence value or probability. Alternately, each voxel which is determined to represent blood tissue, may be given the binary value one and voxels which are determined to represent non-blood tissue may be given the value zero. As yet another alternative, those voxels which are determined to represent non-blood tissue may be given the inverse of their confidence level, i.e. the probability that the voxel does not represent non-blood tissue, i.e. represents blood tissue.

The high contrast or blood image representation is stored in a high contrast image memory means 92.

The growing means D starts at a voxel which is known to be in either the left or right ventricle from the center of mass and second moment determinations made by means 30 and 32. A stepping means 94 reads out the voxel value at the voxel which is known to be in one of the left and right ventricles. The stepping means than moves outward from this voxel, generally in concentric circles, reading the confidence value of each non-zero, contiguous voxel. The stepping means continues to step outward, but only in directions along which blood voxel was found, until all contiguous voxels which have intensities which represent blood are read out or counted. Non-contiguous voxels that are classified as blood tissue may represent other blood vessels rather than the ventricle interior and are not read out. Preferably, slices of the volume image are processed serially. The stepping means determines the initial point of the first slice based on the center of mass. Once the volume of the ventricle in that slice has been determined, the center of mass in that slice can be determined precisely. The stepping means, preferably includes a means for calculating the center of mass of each slice and using the calculated center of mass as the starting point for the next contiguous slice.

A summing means 96 sums the contiguous blood voxel values which the stepping means 94 reads out of the high contrast memory 92. This sum of the confidences is multiplied by the volume of each voxel by multiplying means 98. This product is indicative of the volume of the ventricle, which volume is stored in a ventricle volume memory means 100. The stepping means 94 then steps to a voxel which is predicted from the center mass to be generally centered in the other ventricle and the process repeated.

More specifically to the preferred embodiment, the ventricle volume memory means includes a left ventricle volume memory means 100l and a right ventricle volume memory means 100r. A volume display means 102 converts the stored Ventricle volumes to an appropriate format for display. In the illustrated embodiment, the display means 102 converts the number into an appropriate format to be displayed on a video monitor 104. A slice selecting means 106 enables an operator to select one or more slices of the image representation stored in the high contrast memory means 92 or the subimage memory means 36 to be displayed on the video monitor 104.

The left and right ventricles may not appear as distinct and subregions in every slice and in every cardiac phase. Thus, in slices in which the ventricles appear connected, the stepping means will tend step through both ventricles as it moves from contiguous blood voxel to contiguous blood voxel. An edge operator routine 110 examines the initial image from memory means 20 or the subimage from memory means 36. The high frequency components of the data which was reconstructed by the reconstructing means 12 identifies the interfaces indicative of the edge or boundary between each ventricle and the cardiac tissue. In the preferred embodiment, the edge operator routine 110 uses a sobel edge detector to determine those points lying along the edges. The edge operator based on this analysis defines the edges of each ventricle. The stepping means compares the address of each voxel which it is about to access in the high contrast memory means 92 to determine whether or not it is within or across the edge parameters determined by the edge operator routine 110. Voxels outside of the ventricle volume indicated by the edge operator routine 110 are not accessed or read out to the summing means 96.

A comparing means 112 compares the volumes of the left and right ventricles after the voxels of each slice are summed. By comparing the relative volumes of the left and right ventricles in each slice and by comparing the volumes of each ventricle with the preceding slice or adjacent slices, the comparing means 112 readily determines whether the stepping means has stepped between the two ventricles. When the comparing means determines that the ventricles have been combined, the comparing means enables the stepping means 94 to access the edge operator routine 110 to determine Whether or not it is crossing the ventricle boundaries.

The invention has been described with reference to the preferred embodiment. Obviously, modifications and alterations will occur to others upon reading and understanding the preceding detailed description. It is intended that the invention be construed as including all such modifications and alterations insofar as they come within the scope of the appended claims or the equivalence thereof.

Having thus described the preferred embodiment, the invention is now claimed to be:

1. A method of generating outlines of ventricular volumes, the method comprising:
   non-invasively examining a region of a patient which includes at least one ventricle of a heart, the region being divided into an array of voxels, and generating a first image representation having an intensity value representing each voxel of the region;
   storing the first image representation;
   a time interval after generating the first image representation, non-invasively re-examining the region and generating a second image representation having an intensity value for each voxel of the region;
   storing the second image representation;
   subtracting the intensity values corresponding to common voxels of the first and second image representations to create difference intensity values of a difference image representation in which the difference intensity values corresponding to voxels containing substantially stationary tissue are substantially zero and the difference intensity values corresponding to voxels representing tissues which moved in the time interval between the first and second image representations are not zero, whereby the non-zero intensity values define an edge around the at least one ventricle of the heart.

2. A method of generating outlines of ventricular volumes, the method comprising:
   non-invasively examining a region of a patient which includes at least one ventricle of a heart and generating (1) a first image representation representing the region and (2) a second image representation of the region using a black blood cine technique such that the first and second image representations depict blood tissue in black and non-blood tissue in lighter shades, the first and second image representations being displaced in time;

subtracting the first and second image representations to create a difference image representation in which stationary tissue is depicted substantially in white and tissues which moved in the time between the first and second image representations are displayed in black, whereby the difference image representation depicts a ventricle defining edge in black against a substantially white background.

3. A method of analyzing ventricular volumes, the method comprising:

non-invasively examining a region of a patient which includes a heart and generating (1) a first image representation having intensity values representing voxels of the region and (2) a second image representation having intensity values representing voxels of the region, the first and second image representations being displaced in time;

subtracting the intensity values of the first and second image representations corresponding to like voxels to create intensity values of a difference image representation in which the intensity values of voxels of the first and second image representations representing substantially stationary tissue cancel and the intensity values of the first and second image representations representing tissues which moved between the first and second image representations do not cancel, such that the non-canceling intensity values define an edge around at least one ventricle of the heart; and counting a number of voxels within the ventricle defining edge, the number of counted voxels being proportional to ventricular volume.

4. The method as set forth in claim 3 further including:

determining a confidence value indicative of a probability that each intensity value within the ventricle defining edge represents blood; and weighting each counted voxel in accordance with the confidence value.

5. The method as set forth in claim 4 wherein the step of determining the confidence value includes:

determining a frequency with which each intensity value occurs in voxels of the first image representation within the ventricle defining edge; and determining a deviation between a most commonly occurring intensity value and each other occurring intensity value, the confidence value being proportional to the deviation.

6. A method as set forth in claim 3 wherein the heart includes a left ventricle and a right ventricle and wherein the counting step includes:

independently counting contiguous voxels of the left and right ventricles within a common generally horizontal plane, whereby in planes in which voxels within the left and right ventricle are contiguous, counting the voxels attributable to both the left and the right ventricle as representing the volume of a single one of the left and right ventricles;

comparing a number of voxels counted in each plane with a number of voxels counted in an adjacent plane to determine whether voxels in both the left and right ventricles have been counted as voxels of the single one of the ventricles.

7. A method as set forth in claim 6 further including:

analyzing the first image representation with an edge operator routine to determine an interface between the left and right ventricles; and limiting the counting step to voxels on each side of the determined interface.

8. A method of analyzing ventricular volume comprising:

non-invasively examining a region of a patient which includes at least one ventricle to generate values of voxels of a ventricle image representation;

determining boundary indicative voxels of the ventricle image representation which are indicative of a peripheral boundary of the ventricle;

determining a frequency of occurrence for voxel values of inside voxels disposed within the boundary indicative voxels;

in accordance with the frequency of occurrence of each inside voxel value, determining a probability that each inside voxel value corresponds to blood tissue;

counting the inside voxels and weighting each counted inside voxel in accordance with its determined probability to determine a sum which sum is proportional to the ventricular volume.

9. The method as set forth in claim 8 further including:

comparing voxel values of each outside voxel disposed outside the boundary indicative voxels with a voxel value indicative of lung tissue;

eliminating outside voxels whose voxel values indicate lung tissue;

for at least a portion of remaining outside voxels, determining a frequency of occurrence of each outside voxel value;

determining a probability that each remaining outside value corresponds to non-lung, non-blood tissue in accordance with the determined frequency of occurrence of each outside voxel value.

10. The method as set forth in claim 9 wherein in the probability determining step, the frequency of occurrence determinations are fit to curves, which curves are generally bell shaped and wherein the probability is determined in accordance with deviation of each voxel value from a most frequently occurring voxel value.

11. The method as set forth in claim 10 wherein the counting step includes:

determining an approximate center of the ventricle;

comparing each voxel value with the probability curve for blood tissue;

counting each voxel whose voxel value is indicated by the probability curve as probably being blood tissue;

repeating the comparing and counting steps for voxels contiguous to each counted pixel voxel.

12. The method as set forth in claim 10 wherein the curve fitting step includes:

fitting the frequency of occurrence determination for voxels within the ventricle boundary with a first curve;

subtracting the first curve from a frequency of occurrence determination for voxels both inside and outside of the ventricle boundary to create a frequency of occurrence difference; and fitting a second curve to the frequency of occurrence difference.

13. The method as set forth in claim 12 wherein the curve is one of a Gaussian curve, a lognormal curve, a Maxwell curve, an Erlange curve, a Cauchy curve, a normal curve, and a beta curve.

14. The method as set forth claim 8 wherein the boundary indicative voxels define boundaries of left and right ventricles and wherein some voxels within the boundaries of the left and right ventricles are immediately contiguous, whereby in the counting step, voxels within the boundaries of both the left and right ventricles are counted such that the sum would be indicative of a volume of the left and right ventricles and further including:

determining an inter-ventricle boundary between the left and right ventricles; and during the counting step, restraining counting to opposite sides of the inter-ventricle boundary such that the left and right ventricle volumes are determined individually.

15. The method as set forth in claim 8 wherein the step of determining the boundary indicative voxels includes:

generating first and second images at a time displaced interval;

subtracting the first and second images to create a difference image representation depicting the ventricle boundary and any other subregions which moved in the interval between the first and second images.

16. The method as set forth in claim 8 further including after determining the boundary indicative voxels, determining a subregion of voxels which encompasses the boundary indicative voxels and non-invasively examining the subregion to generate an image representation of the subregion, whereby resolution within the subregion is improved.

17. The method as set forth in claim 8 wherein the step of determining boundary indicative voxels includes:

generating (1) a first image representation representing the region and (2) a second image representation of the region, the first and second image representations being displaced in time;

subtracting the first and second image representations to create a difference image representation in which voxel values corresponding to substantially stationary tissue cancel and voxel values corresponding to tissues which moved between the first and second image representations do not cancel, whereby the non-canceling voxel values define the peripheral boundary of the ventricle.

18. An apparatus for generating outlines of ventricular volumes, the apparatus comprising:

a non-invasive examination means for non-invasively examining a region of a patient which includes ventricles of a heart, the region being divided into a rectangular array of voxels, and generating (1) a first image representation having an intensity value representing each voxel of the region and (2) a second image representation having an intensity value representing each voxel of the region, the first and second image representations being displaced in time;

a subtracting means for subtracting the intensity values corresponding to common voxels of the first and second image representations to create difference intensity values of a difference image representation in which the difference intensity values corresponding to voxels containing substantially stationary tissue cancel and the difference intensity values corresponding to voxels that contain tissues which moved between the first and second image representations do not cancel, whereby the non-cancelling intensity values of the difference image representation represent an edge around ventricles of the heart; and a memory means for storing the difference intensity values of the difference image representation.

19. An apparatus for analyzing ventricular volumes, the apparatus comprising:

a non-invasive examination means for non-invasively examining a region of a patient which includes a heart and generating (1) a first image representation representing the region and (2) a second image representation of the region, the first and second image representations being displaced in time;

a subtracting means for subtracting the first and second image representations to create a difference image representation in which voxel values of voxels of the first and second image representations representing substantially stationary tissue cancel and voxel values of like voxels representing tissues which moved between the first and second image representations do not cancel, whereby the difference image representation represents a surface of non-canceling voxel values around ventricles of the heart;

a counting means for counting a number of voxels within the surface of non-canceling voxel values, the number of counted voxels being proportional to ventricular volume; and, a display means for displaying the ventricular volume.

20. An apparatus for analyzing ventricular volumes, the apparatus comprising:

a non-invasive examination means for non-invasively examining a region of a patient which includes a heart and generating (1) a first image representation representing the region and (2) a second image representation of the region, the first and second image representations being displaced in time;

a subtracting means for subtracting the first and second image representations to create a difference image representation in which voxel values of voxels of the first and second image representations representing substantially stationary tissue cancel and voxel values of like voxels representing tissues which moved between the first and second image representations do not cancel, whereby the difference image representation represents a ventricular edge.

a probability determining means for determining a confidence value indicative of a probability that each voxel value within the ventricular edge defines blood; and a weighting means for weighting each counted voxel in accordance with the confidence value.

21. An apparatus for analyzing ventricular volumes comprising:

a non-invasive examination means for non-invasively examining a region of a patient which includes at least one ventricle to generate intensity values of voxels of a ventricle image representation;

a means for determining which voxels of the ventricle image representation are indicative of a peripheral boundary of the ventricle;

a histogram generating means for determining a frequency of occurrence of the intensity values of voxels surrounded by the ventricle boundary;

a means for determining from the frequency of occurrence a probability that each of the intensity values corresponds to blood tissue;

a counting means for counting voxels surrounded by the ventricle boundary and weighting each counted voxel in accordance with its determined probability to determine a sum which is proportional to the ventricular volume.

22. The apparatus as set forth in claim 21 further including:

a means for comparing intensity values of voxels outside of the ventricle boundary with an intensity value indicative of lung tissue;

a means for subtracting outside voxels whose intensity values indicate lung tissue;

a means for determining a frequency of occurrence of each outside voxel intensity value;

a means for determining a probability that each remaining outside voxel intensity value corresponds to non-lung, non-blood tissue in accordance with the determined frequency of occurrence.

23. The apparatus as set forth in claim 22 wherein the means for determining the ventricle boundary includes:

a means for subtracting first and second images generated at a time displaced interval to create a difference image representation depicting the ventricle boundary.

24. An apparatus for measuring ventricular volumes, the apparatus comprising:

a non-invasive examination means for generating volume image representations of a patient region including its heart;

a means for locating a subregion encompassing the heart;

a means for determining a range of intensity values of voxels of the volume image representations, one of the volume image representations having a range of intensity values corresponding to blood tissue and a range of intensity values corresponding to non-blood tissue;

a means for counting contiguous voxels with intensity values in the intensity value range corresponding to blood tissue, which voxel count is indicative of ventricular volume.

25. The apparatus as set forth in claim 24 wherein the locating means includes a subtracting means for subtracting two of the volume image representations which are generated at a time displaced interval.

26. The apparatus as set forth in claim 24 wherein the range determining means includes a means for fitting a distribution of intensity values in each range to blood and non-blood tissue distribution curves.

27. The apparatus as set forth in claim 24 wherein:

the non-invasive examination means generates intensity values of the voxels of the volume image representations;

the subregion locating means includes a means for determining which voxels of the volume image representations are indicative of a peripheral boundary of the ventricle;

the range of values determining means includes a histogram generating means for determining a frequency of occurrence of intensity values of voxels surrounded by the ventricle boundary and a means for determining from the frequency of occurrence a probability that each intensity value corresponds to blood tissue; and the counting means counts voxels surrounded by the ventricle boundary and wights each counted voxel in accordance with its determined probability to determine a sum which is proportional to the ventricular volume.

28. The apparatus as set forth in claim 27 wherein:

the non-invasive examination means generates (1) a first image representation representing the region and (2) a second image representation of the region, the first and second image representations being displaced in time; and the ventricle boundary voxel determining means includes a subtracting means for subtracting the first and second image representations to create a difference image representation such that intensity values of voxels of the first and second image representation representing substantially stationary tissue cancel and intensity values of voxels representing tissue which moved between the first and second image representations do not cancel, whereby the difference image representation represents the peripheral boundary of the ventricle.

* * * * *